US011324646B2

(12) United States Patent
Crafoord et al.

(10) Patent No.: US 11,324,646 B2
(45) Date of Patent: May 10, 2022

(54) DISPENSER FOR MEDICAL ARTICLES

(71) Applicant: ORKLA CARE AB, Solna (SE)

(72) Inventors: David Crafoord, Bromma (SE); Maria Wik, Årsta (SE)

(73) Assignee: Orkla Care AB, Solna (SE)

( * ) Notice: Subject to any disclaimer, the term of this patent is extended or adjusted under 35 U.S.C. 154(b) by 6 days.

(21) Appl. No.: 15/734,384

(22) PCT Filed: Jun. 5, 2019

(86) PCT No.: PCT/EP2019/064648
§ 371 (c)(1),
(2) Date: Dec. 2, 2020

(87) PCT Pub. No.: WO2019/234098
PCT Pub. Date: Dec. 12, 2019

(65) Prior Publication Data
US 2021/0169712 A1    Jun. 10, 2021

(30) Foreign Application Priority Data

Jun. 8, 2018  (SE) .................................... 1850693-1

(51) Int. Cl.
*A61F 17/00* (2006.01)
*A61F 15/00* (2006.01)
*A47B 67/02* (2006.01)

(52) U.S. Cl.
CPC ............ *A61F 15/001* (2013.01); *A47B 67/02* (2013.01); *A47B 2067/025* (2013.01); *A61F 17/00* (2013.01)

(58) Field of Classification Search
CPC .................................................... A61F 15/001
See application file for complete search history.

(56) References Cited

U.S. PATENT DOCUMENTS

| 2003/0116580 | A1 | 6/2003 | Baughman |
| 2011/0272429 | A1* | 11/2011 | Harfert ................. A61F 15/001 |
|  |  |  | 221/130 |
| 2014/0021215 | A1* | 1/2014 | Tran ........................ B65H 1/08 |
|  |  |  | 221/45 |
| 2014/0034648 | A1 | 2/2014 | Peterson et al. |
| 2020/0306140 | A1* | 10/2020 | Fontaine ............... A61J 7/0069 |

FOREIGN PATENT DOCUMENTS

| CN | 204562589 U | 8/2015 |
| EP | 1695642 A2 | 8/2006 |
| SE | 1550692 A1 | 8/2016 |
| WO | 2006/078200 A1 | 7/2006 |

* cited by examiner

*Primary Examiner* — Gene O Crawford
*Assistant Examiner* — Ayodeji T Ojofeitimi
(74) *Attorney, Agent, or Firm* — Dilworth & Barrese, LLP

(57) ABSTRACT

A dispenser (100) for medical articles (163), comprising a base (110) and a cover (120), wherein the base (110) comprises at least one stopper arrangement (170) integrated in the main wall of the base (110) and protruding from the inside surface (111b) of the main wall of the base (110), wherein each of the at least one stopper arrangement (170) has at least one cut-out (171) configured to to hold medical articles (163), received in a respective opening in the cover (120) when the dispenser (100) is in a closed configuration, and configured to release receive and hold at least one medical article (163), or a container (160) configured its hold on the at least one medical article (163) or the container (160) when the dispenser (100) is in an open configuration.

20 Claims, 9 Drawing Sheets

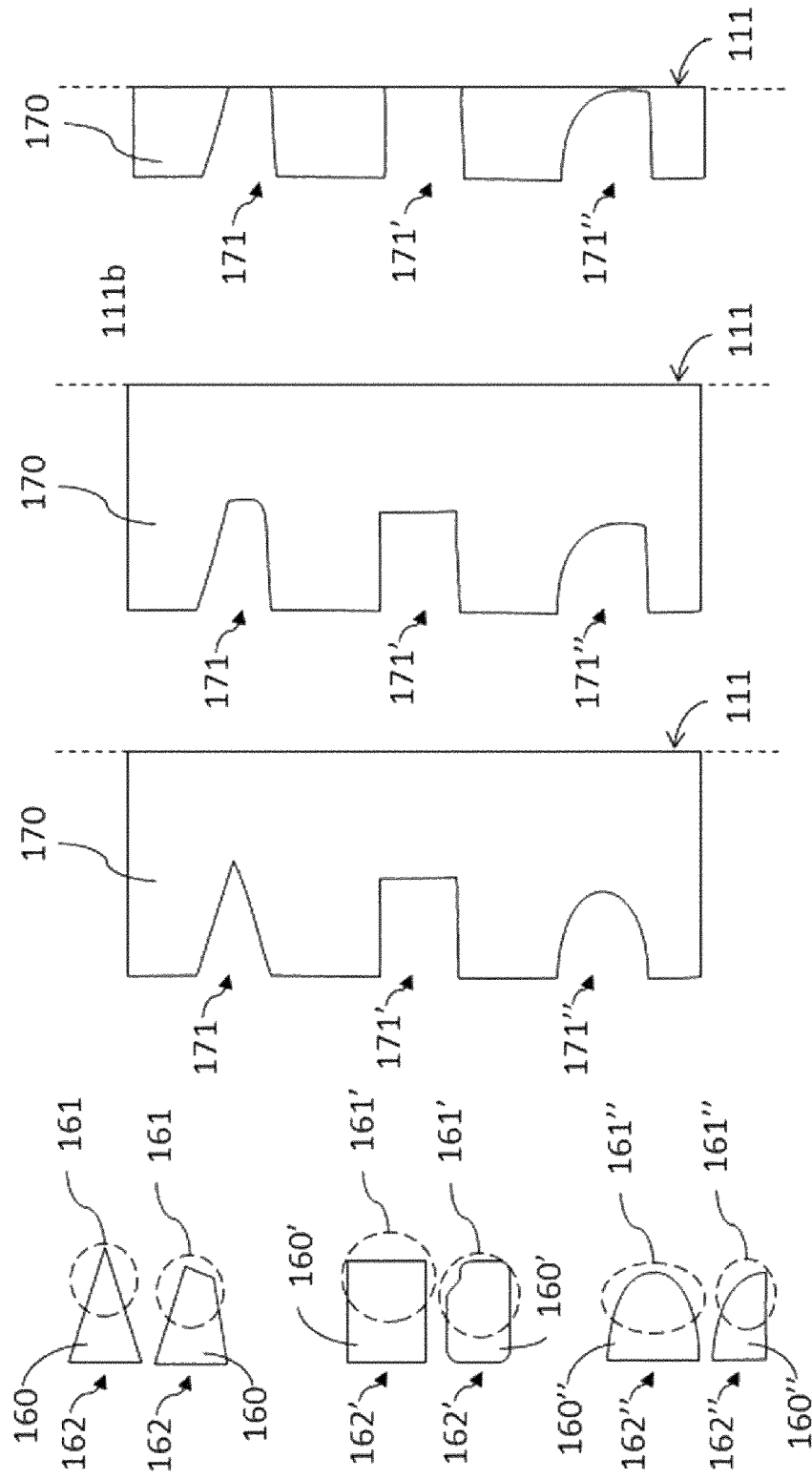

DISPENSER FOR MEDICAL ARTICLES

FIELD OF THE DISCLOSURE

The present disclosure relates to dispensers for medical articles, more particularly to dispensers for disposable medical articles, such as wound care articles.

BACKGROUND OF THE DISCLOSURE

Dispensers for medical articles known in the art are typically first aid cabinets comprising different compartments which can hold and deliver medical articles. Disposable medical articles can normally be pulled out of or otherwise removed from the dispenser or cabinet. Small-sized medical articles, such as plasters, are commonly stored together in a container, which can be inserted into a compartment of the dispenser. It is known in the art to structure such a compartment to receive and hold a container comprising a plurality of small-sized medical articles when the dispenser is closed. To avoid unwanted removal of the container, the compartment or the dispenser comprises elements which keep the container in place when the dispenser is closed. In order to remove a container, e.g. to enable refilling of a new container, either the entire dispenser or the individual compartment has to be opened or unlocked. One solution known in the art is to unlock a compartment by inserting a specially adapted key in the front part of the dispenser to unlock the container. Other known solutions involve unlocking and/or opening the entire dispenser to remove the container from the inside of the dispenser. Different types of known dispensers for medical articles are described for example in European Patent EP1695642 B1, U.S. Pat. No. 9,254,229 B2, U.S. Pat. No. 3,189,219 and U.S. Design Pat. No. D652,662 S.

Removal of containers comprising medical articles and refilling of dispensers should preferably be made easy and time efficient. In the cabinet described in EP1695642 B1, removing a container requires that the user opens the cabinet, pushes the container into position for removal using for example an index finger of a first hand, and reaches into the compartment from the inside of the cabinet to pull out the container using a second hand. This requires several subsequent actions and the use of two hands, which is not optimal for example if the user has limited mobility. It is desirable to further streamline and facilitate the removal of containers from dispensers for medical articles.

SUMMARY OF THE DISCLOSURE

The above objective to further streamline and facilitate the removal of containers from dispensers for medical articles is achieved by the present disclosure, which relates to a dispenser for medical articles, wherein the dispenser comprises a base comprising stopper arrangements and a cover pivotally mounted on the base and configured to receive containers adapted to hold a plurality of medical articles. The stopper arrangements correspond in shape and position to the containers such that the stopper arrangements hold the containers in place when the dispenser is closed. When the dispenser is open, the containers are accessible and removable in a simple manner, such as by using a one-hand grip. The removal of containers is facilitated since the stopper arrangements are located on the base and therefore are not blocking removal of the containers located in the cover once the dispenser is opened.

More particularly, the present disclosure is directed to a dispenser for medical articles, comprising:
- a base comprising a main wall having an outside surface and an inside surface, a top wall, a first side wall, a second side wall, and a bottom wall; and
- a cover comprising a main wall having an outside surface and an inside surface, a top wall having an outside surface and an inside surface, a first side wall, a second side wall, and a bottom wall;
- wherein the bottom wall of the base and the bottom wall of the cover are arranged to be attachable to each other, wherein the base and the cover, when attached to each other, are arranged to be tiltable in relation to each other around a first axis;
- wherein the top wall of the base and the top wall of the cover are arranged to be detachably attachable to each other, such that the dispenser is in a closed configuration and the base and cover form a closed space when the top wall of the base and the top wall of the cover are attached to each other, and such that the dispenser is in an open configuration when the top wall of the base and the top wall of the cover are not attached to each other;
- wherein the cover comprises at least one opening in its main wall, which at least one opening is adapted to receive at least one medical article or a container configured to hold at least one medical article, such that, when at least one medical article or a container comprising at least one medical article is located in an opening, the at least one medical article is accessible from the outside of the main wall of the cover via the opening;
- characterised in that the base comprises at least one stopper arrangement integrated in the main wall of the base and protruding from the inside surface of the main wall of the base, wherein each of the at least one stopper arrangement has at least one cut-out configured to receive and hold a medical article or a container received in a respective opening of the main wall of the cover when the dispenser is in a closed configuration, and is configured to release its hold on the medical article or the container when the dispenser is in an open configuration.

Preferred aspects of the present disclosure are described in the dependent claims.

DETAILED DESCRIPTION OF THE DISCLOSURE

The figures illustrate various configurations of dispensers and parts thereof according to the present disclosure. It is to be understood that the figures are schematic drawings only; not necessarily showing correct ratios between the different elements. Further, a dispenser according to the present disclosure can comprise any suitable number of openings in the cover of the dispenser and any suitable number of corresponding cut-outs in the stopper arrangements integrated in the base of the dispenser. The number and configurations of openings and cut-outs shown in each figure should not be construed as limiting the dispenser to consist of the exact number and configuration of openings and cut-outs shown. Preferably, as shown in the figures herein, the top walls and the bottom walls of both the base and the cover are substantially parallel to each other, the side walls of both the base and the cover are substantially parallel to each other, and the side walls are essentially perpendicular to the top walls and the bottom walls. However, it is to be understood that one or more of the top walls and/or the bottom walls may be non-parallel to the other top wall(s) and bottom wall(s), and further that one or more of the side walls may be non-parallel to the other side walls and/or may be non-perpendicular to one or more of the top walls and/or one or more of the bottom walls. Further, although the corners of the dispenser have been shown as straight corners in the figures herein, it is to be understood that the dispenser could have one or more rounded corners instead. Also, the number and configurations of the optional partitioning walls shown in some figures should not be construed as limiting the dispenser to consist of the exact number and configuration of partitioning walls shown. The figures should merely be seen as examples of how dispensers according to the present disclosure can be constructed. However, in each configuration the height and width of the base should correspond substantially to the height and width of the cover.

FIG. 1 shows different views of non-limiting configurations of a dispenser 100 according to the present disclosure. The dispenser 100 is adapted to hold and deliver medical articles 163, which are optionally stored in a container 160. Medical articles 163 to be stored in the dispenser 100 may for example be disposable medical articles, such as disposable wound care articles, e.g. plasters, gauze etc.

Figures 1A, 1B:
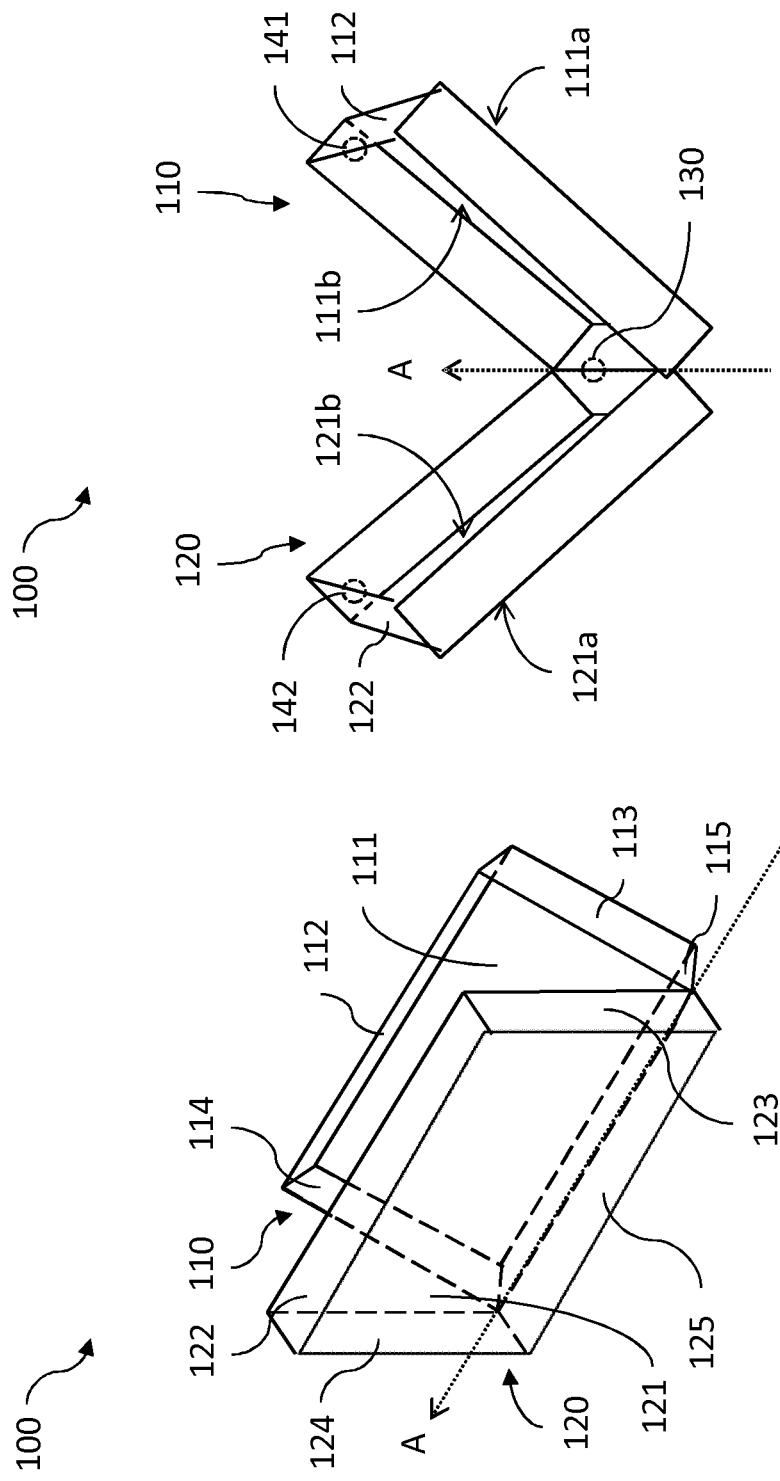
FIG. 1 shows different views of non-limiting configurations of a dispenser according to the present disclosure.

FIG. 1a is a perspective view of a dispenser 100 according to the present disclosure. The dispenser 100 comprises a base 110 and a cover 120. The base 110 comprises a main wall 111, a top wall 112, a first side wall 113, a second side wall 114, and a bottom wall 115. The cover 120 comprises a main wall 121, a top wall 122, a first side wall 123, a second side wall 124, and a bottom wall 125. The base 110 and the cover 120 are arranged to be attachable to each other, wherein the base 110 and the cover 120, when attached to each other, are arranged to be tiltable in relation to each other around a first axis A. In FIG. 1a the dispenser 100 is in an open configuration.

According to a non-limiting configuration, the base 110 may be adapted to be mounted on a wall or another at least substantially vertical surface with the top wall 112 of the base 110 located upwards and the bottom wall 115 of the base 110 located downwards in relation to the at least substantially vertical surface, and wherein the bottom wall 125 of the cover 120 may be said to be pivotally mounted on the bottom wall 115 of the base 110. In some embodiments, the cover 120 may be configured to pivot or tilt a maximum of 90° from the base 110. Advantageously, this may hinder any medical articles 163 and/or containers 160 from accidentally falling out of the cover 120 when the dispenser 100 is in an open configuration.

It is to be understood that terms like "bottom wall", "top wall", "top edge", bottom edge" refer to the relative positions of the wall(s) or edge(s), respectively, when the base 110 of the dispenser 100 is mounted on a wall or another at least substantially vertical surface with the bottom wall 115 downwards and the top wall 112 upwards, or when the dispenser 100 is standing on a horizontal surface, with the bottom walls 115 and 125 downwards and the top walls 112 and 122 upwards.

Terms like "vertical" and "horizontal" also refer to relative directions or positions of elements when the base 110 of the dispenser 100 is mounted on a wall or another at least substantially vertical surface with the bottom wall 115 downwards and the top wall 112 upwards, or when the dispenser 100 is standing on a horizontal surface, with the bottom walls 115 and 125 downwards and the top walls 112 and 122 upwards.

FIG. 1b is a perspective view of a dispenser 100 according to the present disclosure, wherein the dispenser 100 is in an open configuration. The dispenser 100 comprises a base 110 and a cover 120. The base 110 comprises a main wall having an outside surface 111a and an inside surface 111b. The cover 120 comprises a main wall having an outside surface 121a and an inside surface 121b. The base 110 and the cover 120 are arranged to be attachable by one or more first attachment means 130 located along the first axis A, wherein each of the one or more first attachment means 130 for example comprises a first attachment element located approximately at, or in the vicinity of, an edge of the bottom wall 115 of the base 110 and a second attachment element located approximately at, or in the vicinity of, an edge of the bottom wall (125) of the cover (120) being configured to be attachable to each other. FIG. 1b shows one first attachment means 130, for illustrative purposes only. It is to be understood that different attachment techniques can be used to attach the bottom wall 115 of the base 110 to the bottom wall 125 of the cover 120. In some embodiments, the attachment mechanism may be configured to allow the cover to rotate a maximum of 90° from the base. Advantageously, this may hinder any medical articles 163 and/or containers 160 from accidentally falling out of the cover 120 when the dispenser 100 is in an open configuration.

As shown in FIG. 1b, the base 110 and the cover 120 are arranged to be detachably attachable by one or more second attachment means (140, shown in FIG. 1c), preferably wherein each second attachment means comprises a third attachment element 141 located at the base 110, for example located at the top wall 112 of the base 110, and preferably a fourth attachment element 142 located at the cover 120, for example located at the top wall 122 of the cover 120. The third attachment element 141 and the fourth attachment element 142 may be located on the outside of the dispenser 100, inside the dispenser 100, at the edge of the top walls 112 and 122, respectively, or located according to any other suitable configuration enabling the top wall 112 of the base 110 and the top wall 122 of the cover 120 to be detachably attachable to each other. It is to be understood that different attachment techniques or closing mechanisms can be used to attach the top wall 112 of the base 110 to the top wall 122 of the cover 120.

Figure 1C:
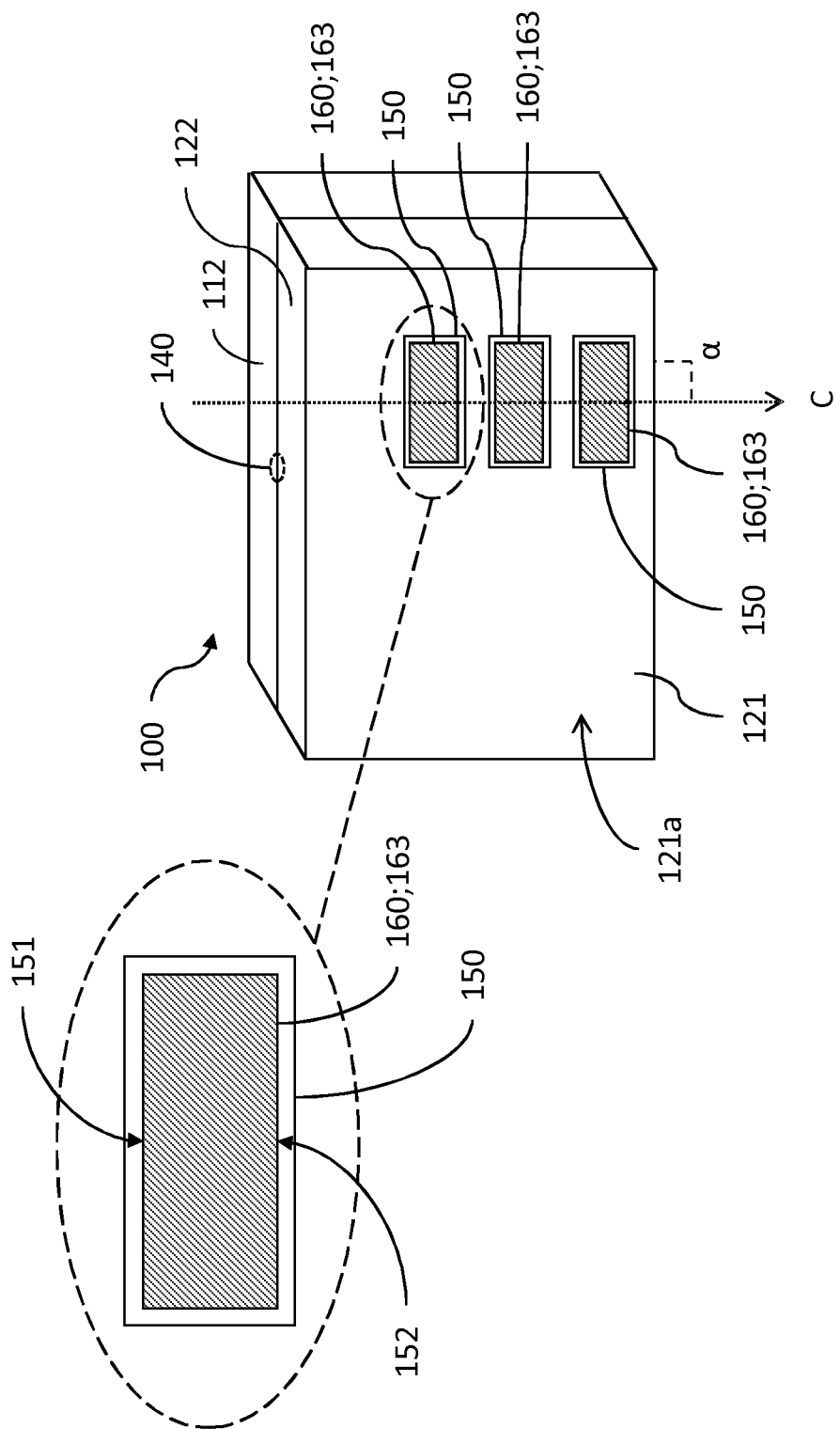

FIG. 1c shows a perspective view of a dispenser 100 seen from the outside surface 121a of the main wall 121 of the cover 120, and further shows a detailed front view of an opening 150. In FIG. 1c, the top wall 112 of the base 110 and the top wall 122 of the cover 120 are attached to each other by one or more second attachment means 140, such that the base 110 and the cover 120 form a closed space, such that the dispenser 100 is in a closed configuration. FIG. 1c shows one second attachment means 140, for illustrative purposes only. The cover 120 comprises at least one opening 150 in its main wall 121. FIG. 1c shows three openings, for illustrative purposes only. The at least one opening 150 of the main wall 121 of the cover 120 is adapted to receive at least one medical article 163 or a container 160. As seen in the detailed view in FIG. 1c of the opening 150, each opening 150 has a top edge 151 and a bottom edge 152. The at least one opening 150 in the cover 120 can be placed at any position of the main wall 121. Further, each opening 150, here depicted as being rectangular in shape, can have any suitable size and shape adapted to receive a respective at least one medical article 163 or a respective container 160 of any corresponding size and shape. The cover 120 may comprise any suitable number of openings 150, such as at least two openings 150 in the main wall 121, such as 2, 3, 4, 5, 6, 7, 8, 9, 10, 20, 30, 40, or 50 openings 150. As seen in FIG. 1c, the centers of the at least two openings may be located along a third axis C, wherein the third axis C is at an angle α to the top wall 122 and to the bottom wall 125 of the cover 120. It is to be understood that the number of openings 150 included in a cover 120, and/or the properties of each opening 150, can be varied and adapted depending on the intended application.

In some embodiments, the third axis C may be perpendicular or essentially perpendicular to the top wall 122 and the bottom wall 125, i.e. the angle α being about 90°. This is illustrated in the example of FIG. 1c. According to these embodiments, the openings are located in a row with their centers substantially straight above each other, as seen when viewing the outside surface 121a of the main wall 121 of the cover 120, the dispenser standing on a horizontal surface or hanging on a vertical wall.

FIG. 2 illustrates different views of non-limiting configurations of a cover 120 and details of a cover 120, which is part of a dispenser 100 according to the present disclosure.

Figure 2A:
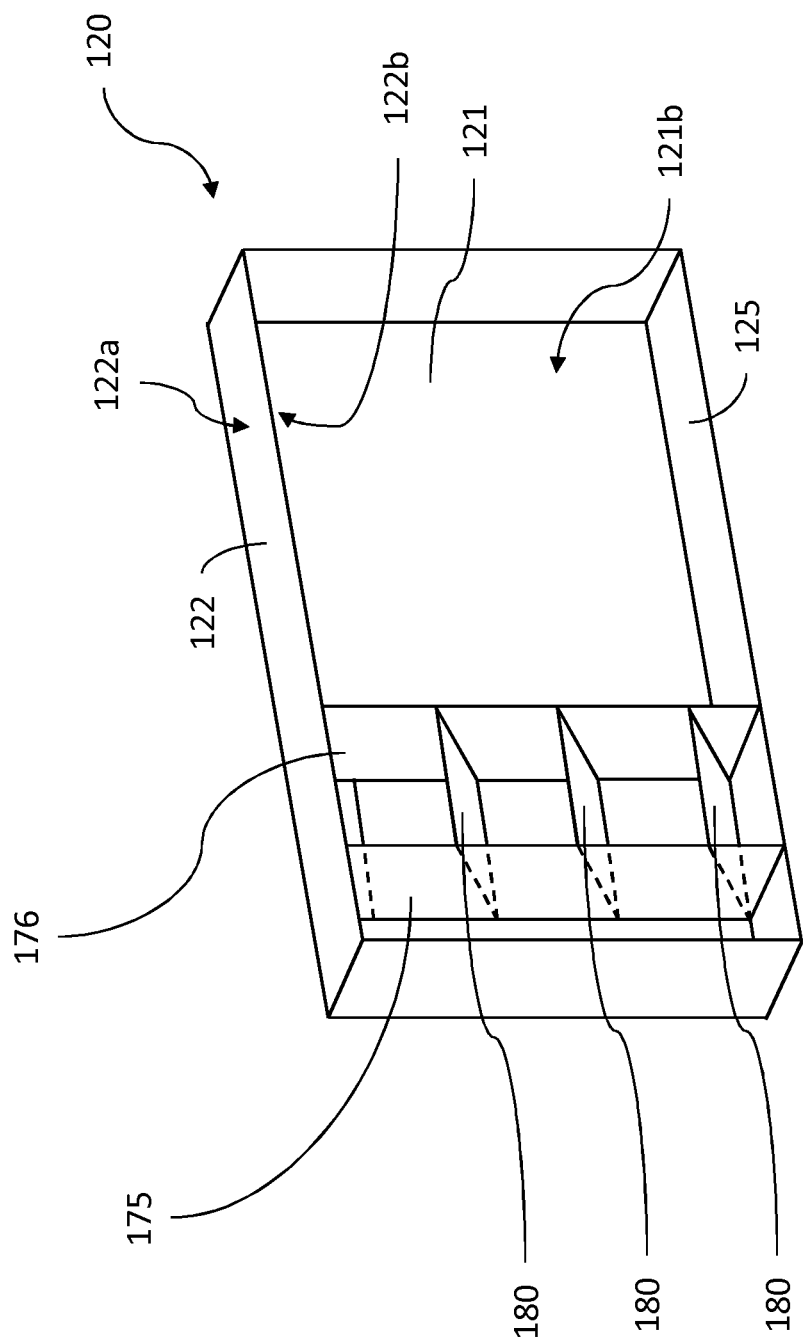
FIG. 2 illustrates different views of non-limiting configurations of a cover and details of a cover, which is part of a dispenser according to the present disclosure.

FIG. 2a is a perspective view of a cover 120 seen from the inside surface 121b of the main wall 121 of the cover 120. The top wall 122 of the cover has an outside surface 122a and an inside surface 122b. As depicted in FIG. 2a, the cover 120 may optionally comprise a first partitioning wall 175, which extends at least a part of the distance between the top wall 122 and the bottom wall 125 of the cover 120. The first partitioning wall 175 is preferably positioned essentially perpendicular to the top wall 122 and/or to the bottom wall 125 of the cover 120, more preferably essentially perpendicular to the top wall 122 and to the bottom wall 125. As shown in FIG. 2a, the cover 120 may optionally further comprise a second partitioning wall 176, which extends at least a part of the distance between the top wall 122 and the bottom wall 125 of the cover 120. The second partitioning wall 176 is preferably positioned essentially perpendicular to the top wall 122 and/or to the bottom wall 125 of the cover 120, more preferably essentially perpendicular to the top wall 122 and to the bottom wall 125. The first partitioning wall 175 and the second partitioning wall 176 are preferably parallel to each other.

One or more of the at least one opening 150 may extend between any first set of two neighbouring walls selected from the first side wall 123 of the cover 120, the second side wall 124 of the cover 120, the optional first partitioning wall 175, and the optional second partitioning wall 176. In embodiments wherein the cover 120 comprises at least two openings 150, one or more of the at least two openings 150 may extend between any first set of two neighbouring walls selected from the first side wall 123 of the cover 120, the second side wall 124 of the cover 120, the optional first partitioning wall 175, and the optional second partitioning wall 176, and/or one or more of the at least two openings 150 may extend between any second set of two neighbouring walls selected from the first side wall 123 of the cover 120, the second side wall 124 of the cover 120, the optional first partitioning wall 175, and the optional second partitioning wall 176. It is to be understood that in such embodiments the first set of neighbouring walls is different from the second set of neighbouring walls, and thus that the "one or more openings 150" referred to as extending between the first set of neighbouring walls are different from the "one or more openings 150" referred to as extending between the second set of neighbouring walls.

Alternatively to, or in combination with, the above-described embodiments, the cover 120 may comprise at least one additional partitioning wall extending at least a part of the distance between the top wall 122 and the bottom wall 125 of the cover 120, said at least one partitioning wall preferably being essentially perpendicular to the top wall 122 and the bottom wall 125 of the cover 120. In these embodiments, there are at least two openings 150 in the main wall 121, such as 2, 3, 4, 5, 6, 7, 8, 9, 10, 20, 30, 40, or 50 openings 150, wherein at least one first of the at least two openings 150 extends between a first set of two neighboring walls selected from the first side wall 123 of the cover 120, the second side wall 124 of the cover 120, the first partitioning wall 175, the second partitioning wall 176 and the at least one additional partitioning wall, and wherein at least one second of the at least two openings (150) extends between a second set of two neighbouring walls selected from the first side wall (123) of the cover (120), the second side wall (124) of the cover (120), the first partitioning wall (175), the optional second partitioning wall (176) and the optional at least one additional partitioning wall. It is to be understood that the first set of neighbouring walls is different from the second set of neighbouring walls. In cases where the cover 120 comprises at least three openings 150, these embodiments may be combined with the embodiments described above in connection to FIG. 1c, wherein the centers of at least two openings 150 are located along the third axis C. Thus, in such cases the "at least two openings 150" referred to in each of the embodiments cannot both be the same two openings 150.

In summary, at least two openings 150 may be located in a substantially vertical row, i.e. with their centers substantially straight above each other, and/or at least two openings 150 may be located in a substantially horizontal row and/or at least one of the at least two openings 150 and at least one other opening 150 of the at least two openings 150 may be located with their centers displaced compared to each other in the horizontal direction as well as in the vertical direction, as seen when viewing the outside surface 121a of the main wall 121 of the cover 120, the dispenser standing on a horizontal surface or hanging on a vertical wall. In other words, in embodiments where the cover 120 comprises two openings 150, the openings 150 can be placed diagonally, vertically or horizontally in relation to each other, and when the cover 120 comprises more than two openings 150, the openings 150 can be placed diagonally, vertically and/or horizontally in relation to each other.

Figure 2B:
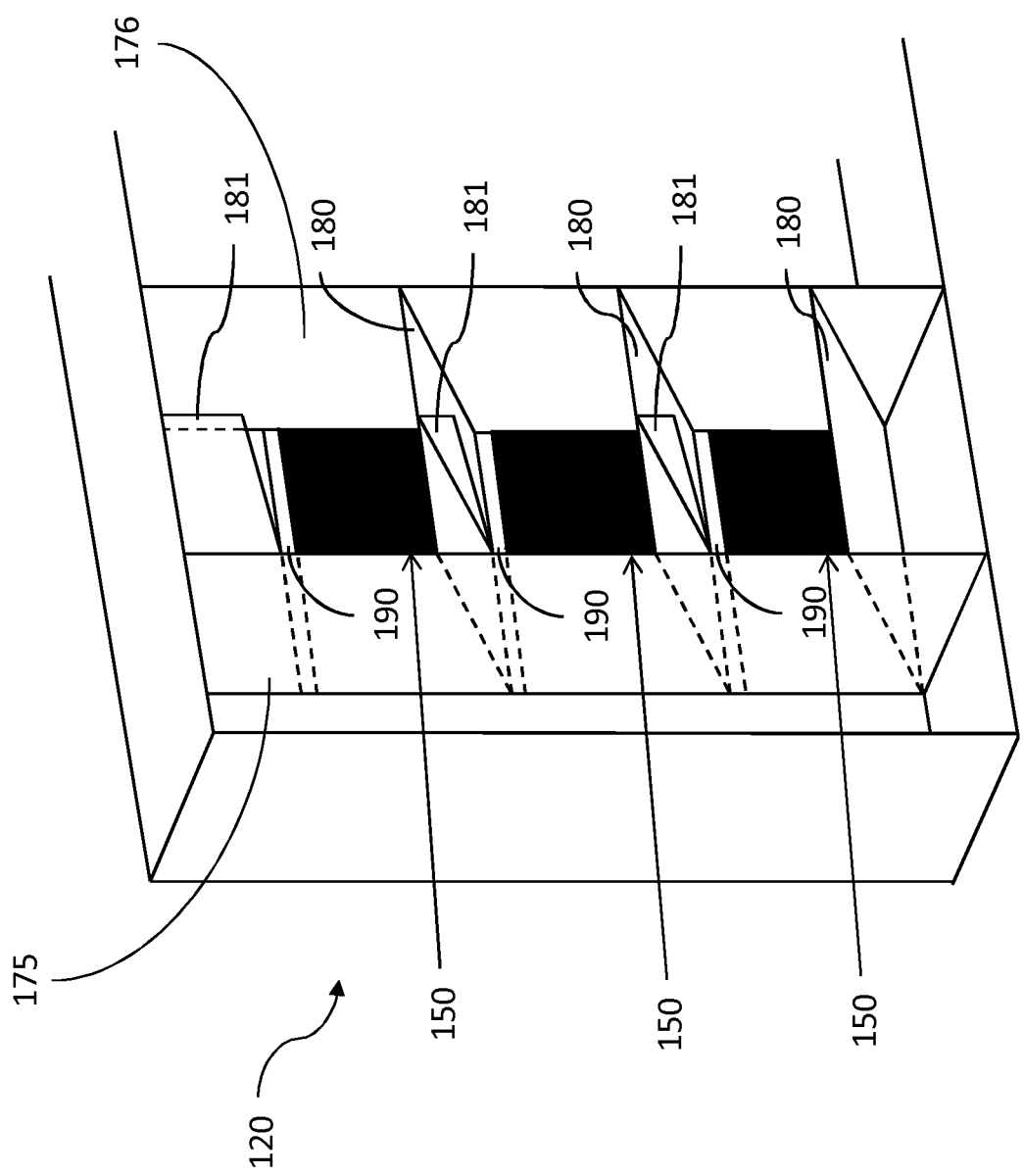
Figure 2C:
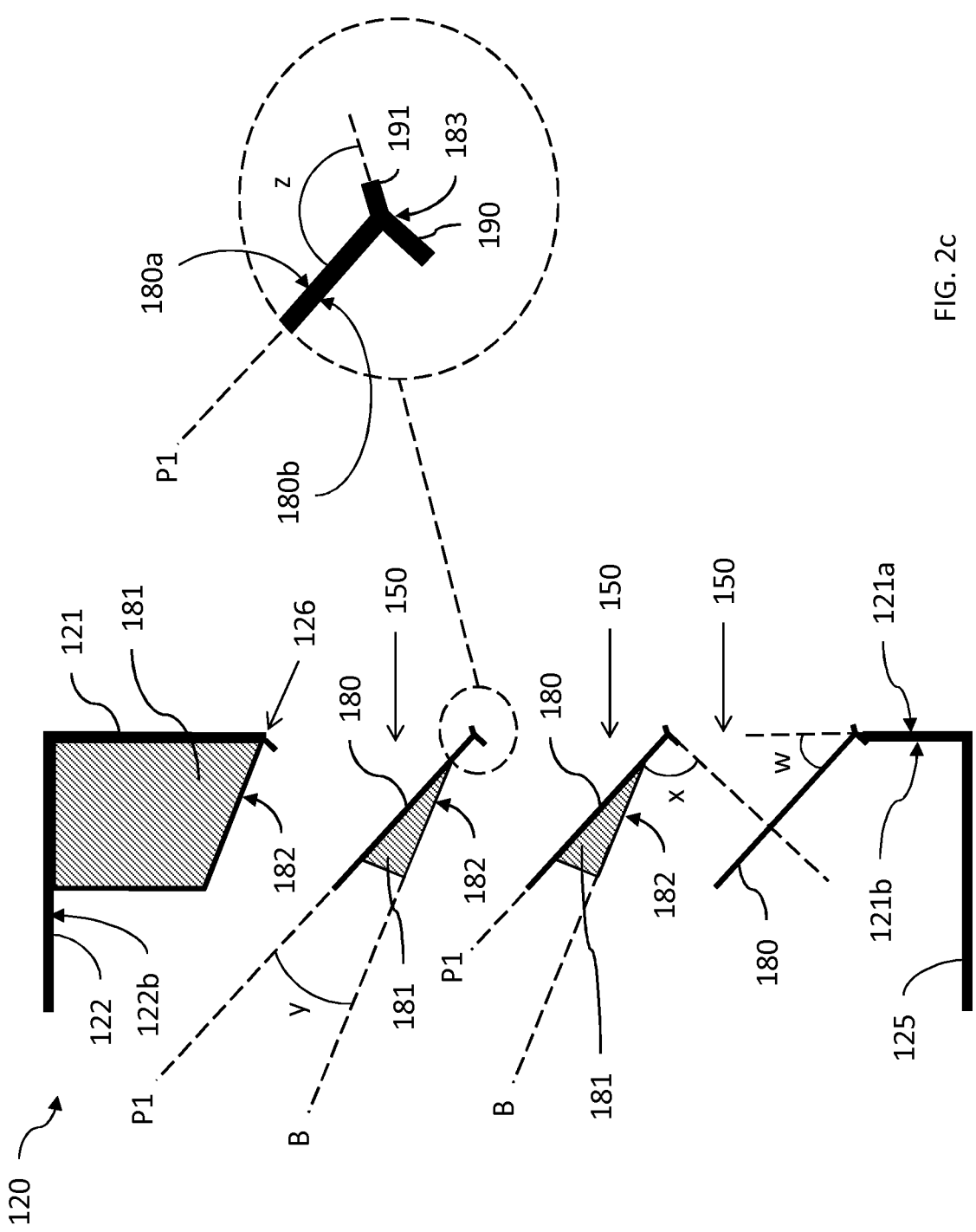

As illustrated in FIG. 2c, the cover 120 may optionally comprise at least one first guiding element 180. FIG. 2a shows three first guiding elements 180, for illustrative purposes only. If present in the dispenser 100, the at least one first guiding element 180 extends between two neighbouring walls selected from the first partitioning wall 175 and the second partitioning wall 176, and is fixed to the first partitioning wall 175 and to the second partitioning wall 176.

FIG. 2b is a more detailed perspective view of a part of the cover 120 shown in FIG. 2a. The optional at least one guiding element 180 is configured to guide at least one medical article 163 or a container 160 (not shown in FIG. 2b) into a respective opening 150. The optional at least one guiding element 180 may extend between any set of two neighbouring walls selected from the first side wall 123 of the cover 120, the second side wall 124 of the cover 120, the optional first partitioning wall 175, and the optional second partitioning wall 176, for example between the first partitioning wall 175 and the second partitioning wall 176 as illustrated in FIG. 2b. The first guiding element 180 is not essential to keep a medical article 163 or a container 160 in place in a respective opening 150 when the dispenser 100 is in the closed configuration, but may further improve this function.

As further depicted in FIG. 2b, the cover 120 may optionally further comprise at least one second guiding element 181. FIG. 2b shows three openings 150, three corresponding first guiding elements 180, and three corresponding second guiding elements 181, for illustrative purposes only. The second guiding element 181 will be described in more detail further below.

As a non-limiting example, FIG. 2c depicts a cross section of an exemplary cover 120 along axis C as shown in FIG. 1c, which cross section shows the main wall 121 having an outside surface 121a and an inside surface 121b, the top wall 122 having an inside surface 122b and the bottom wall 125 of the cover 120. Further depicted is the optional at least one first guiding element 180, extending in a first plane P1 at an angle w of from 10° to 170°, preferably from 20° to 90°, more preferably from 30° to 70°, to the main wall 121 of the cover 120. It is to be understood that there is one first plane P1 per first guiding element 180. In embodiments where the cover 120 comprises at least two first guiding elements 180, the corresponding at least two first planes P1 are preferably essentially parallel to each other, as illustrated in FIG. 2c.

The optional at least one first guiding element 180 may have a first surface 180a facing towards the top wall 122 and a second surface 180b facing away from the top wall 122, and further may have a first edge 183, which may protrude in the first plane P1 towards the outside surface 121a of the cover 120, as shown in the detailed view of FIG. 2c.

As a non-limiting example, the detailed view of FIG. 2c shows that the cover 120 further may comprise at least one first blocking element 190 configured to engage at least one medical article 163 or a container 160 located in a respective at least one opening 150 so as to hinder the at least one medical article 163 or the container 160 from falling out of or being removed from the dispenser 100 through the respective at least one opening 150 from the outside of the cover 120.

The optional at least one first blocking element 190 may be fixed to and protrude from the main wall 121, preferably being fixed to and protruding approximately from a first edge 126 of the main wall 121, away from the inside surface 121b of the main wall 121, or may be fixed to and protrude from a first guiding element 180, preferably being fixed to and protruding approximately from a first edge 183 of the first guiding element 180, away from the second surface 180b of the first guiding element 180, at an angle x of from 50° to 110°, preferably from 50° to 90°, more preferably from 70° to 90°, to the first plane P1 or a plane parallel to the first plane P1. The first blocking element 190 is not essential to keep a medical article 163 or a container 160 in place in a respective opening 150 when the dispenser 100 is in the closed configuration, but may further improve this function.

It is to be understood that since the optional one or more first blocking element 190 may be fixed to and protrude from the main wall 121 at an angle x as described in more detail above, preferably being fixed to and protruding approximately from a first edge 126 of the main wall 121 at an angle x as described in more detail above the at least one first blocking element 190 may be located approximately at, or in the vicinity of, the top edge 151 (see FIG. 1c) of the respective at least one opening 150 located directly below the first edge 126 of the main wall 121, as seen when viewing the outside surface 121a of the main wall 121 of the cover 120, the dispenser standing on a horizontal surface or hanging on a vertical wall.

Further, it is to be understood that since the optional one or more first blocking element 190 may be fixed to and protrude from a first guiding element 180 at an angle x as described in more detail above, preferably being fixed to and protruding from a first edge 183 of an at least one first guiding element 180 at an angle x as described in more detail above, consequently the at least one first blocking element 190 may be located approximately at, or in the vicinity of, the top edge 151 (see FIG. 1c) of the respective at least one opening 150 located directly below the first edge 183 of the respective first guiding element 180, as seen when viewing the outside surface 121a of the main wall 121 of the cover 120, the dispenser standing on a horizontal surface or hanging on a vertical wall.

Each of the at least one first blocking element(s) 190 may be of any suitable size and shape to block removal or falling out of a respective at least one medical article 163 or a respective container 160 from the outside of the cover 120. Further, one or more of the at least one optional first blocking element(s) 190 may be located at any position along the edge 126 of the main wall 121 and/or at any position along the edge 183 of a first guiding element 180. As a non-limiting example, the cover 120 may comprise at least one, such as 1, 2, 3, 4, 5, 6, 7, 8, 9, or 10 first blocking elements 190 being fixed to and distributed along the first edge 183 of each of the at least one first guiding elements 180 and protruding from the first edge 183 of the first guiding element 180, away from the second surface 180b of the first guiding element 180, at an angle x of from 50° to 110°, preferably from 50° to 90°, more preferably from 70° to 90°, to the first plane P1 or a plane parallel to the first plane P1. For example, the at least one first guiding element 180 may have one first blocking element 190 fixed approximately at the center of its first edge 183, or the at least one first guiding element 180 may have two first blocking elements 190 fixed at its first edge 183, distributed close to or at the outermost areas of the first edge 183, or the at least one first guiding element 180 may have a combination of three first blocking elements 190 fixed to its first edge 183, wherein the three first blocking elements 190 are distributed evenly or unevenly along the first edge 183, e.g. distributed approximately at the center and close to or at the outermost areas of the first edge 183.

It is to be understood that as an alternative, or in combination with the above-described embodiments, one or more of the at least one optional first blocking element(s) 190 may extend between and be fixed to any set of two neighbouring walls selected from the first side wall 123 of the cover 120, the second side wall 124 of the cover 120, the first partitioning wall 175, the second partitioning wall 176, and the optional at least one additional partitioning wall (not shown), in any suitable manner that enables the first blocking element 190 to engage at least one medical article 163 or a container 160 located in a respective at least one opening 150, so as to hinder the at least one medical article 163 or the container 160 from falling out of the dispenser 100 through the respective opening 150 or being removed from the dispenser 100 from the outside of the cover 120. According to another alternative embodiment, a first blocking element 190 may be fixed to a first wall selected from the first side wall 123 of the cover 120, the second side wall 124 of the cover 120, the optional first partitioning wall 175, the optional second partitioning wall 176 and the optional at least one additional partitioning wall, and protrude towards a second, neighbouring wall selected from the first side wall 123 of the cover 120, the second side wall 124 of the cover 120, the optional first partitioning wall 175, the optional second partitioning wall 176, and the optional at least one additional partitioning wall, in any suitable manner that enables the first blocking element 190 to engage at least one medical article 163 or a container 160 located in a respective opening 150, so as to hinder the at least one medical article 163 or the container 160 from falling out of the dispenser 100 through the respective opening 150 or being removed from the dispenser 100 from the outside of the cover 120.

In a currently preferred embodiment, a first blocking element 190 is fixed to and protrudes from a first edge 126 of the main wall 121 away from the inside surface 121b of the main wall 121, or is fixed to and protrudes from a first edge 183 of a first guiding element 180 away from the second surface 180b of the first guiding element 180, and said first blocking element 190 further extends between and is fixed to a set of two neighbouring walls selected from the first side wall 123 of the cover 120, the second side wall 124 of the cover 120, the optional first partitioning wall 175, the optional second partitioning wall 176, and the optional at least one additional partitioning wall, at an angle x of from 50° to 110°, preferably from 70° to 90°, to the first plane P1 or a plane parallel to P1 (not shown).

FIG. 2c further illustrates that the cover 120 may optionally comprise at least one second guiding element 181, which may be fixed to the second surface 180b of a first guiding element 180, or which may be fixed to the inside surface 122b of the top wall 122 and/or to the inside surface 121b of the main wall 121 of the cover 120. The optional second guiding element 181 may have a guiding edge 182, which may extend along a second axis B at an angle y of from 15° to 30°, preferably from 20° to 25°, to the first plane P1. The second guiding element 181 is not essential to achieve the main object of the present disclosure, but may further improve this function.

It is to be understood that there is one second axis B per second guiding element 181. In embodiments where the cover 120 comprises at least two second guiding elements 181, the corresponding at least two second axes B are preferably essentially parallel to each other.

As shown in FIG. 2c, the cover 120 may optionally further comprise at least one second blocking element 191, configured to further engage at least one medical article 163 or a container 160 located in a respective at least one opening 150 so as to hinder the at least one medical article 163 or the container 160 from falling out of or being removed the dispenser 100 through the respective opening 150 from the outside of the cover 120. The optional at least one second blocking element 191 may be fixed to a first edge 183 of a respective first guiding element 180 and may protrude from the first surface 180a of the first guiding element 180 at an angle z of from 50° to 100°, preferably from 60° to 95°, to the first plane P1. The second blocking element 191 is not essential to achieve the main object of the present disclosure, but may further improve this function.

It is to be understood that there may be one or more optional second blocking element(s) 191 fixed to and protruding from the first edge 183 of each of the at least one first guiding element 180 at an angle z as described in more detail above. In other words, each of the one or more said second blocking elements 191 may be located approximately at, or in the vicinity of, the bottom edge 152 (see FIG. 1c) of the respective at least one opening 150 located directly above the first edge 183 of the respective first guiding element 180, as seen when viewing the outside surface 121a of the main wall 121 of the cover 120, the dispenser standing on a horizontal surface or hanging on a vertical wall.

Each of the optional at least one second blocking element(s) 191 may be of any suitable size and shape to further block removal or falling out of a respective at least one medical article 163 or a respective container 160 from the outside of the cover 120. Further, each of the at least one optional first blocking element(s) 191 may be located at any position along the edge 183 of a first guiding element 180. As a non-limiting example, the cover 120 may comprise at least one, such as 1, 2, 3, 4, 5, 6, 7, 8, 9, or 10 second blocking elements 191 being fixed to and distributed along the first edge 183 of each of the at least one first guiding elements 180 and protruding from the first surface 180a of the first guiding element 180 at an angle z of from 50° to 100°, preferably from 60° to 95°, to the first plane P1. For example, the at least one first guiding element 180 may have one second blocking element 191 fixed approximately at the center of its first edge 183, or the at least one first guiding element 180 may have two second blocking elements 191 fixed at its first edge 183, distributed close to or at the outermost areas of the first edge 183, or the at least one first guiding element 180 may have a combination of three second blocking elements 191 fixed to its first edge 183, wherein the three second blocking elements 191 are distributed evenly or unevenly along the first edge 183, e.g. with one of them being located approximately at the center and the other two being placed close to or at the outermost areas of the first edge 183.

It is to be understood that as an alternative, or in combination with the above-described embodiments, one or more of the at least one optional second blocking element(s) 191 may extend between and be fixed to any set of two neighbouring walls selected from the first side wall 123 of the cover 120, the second side wall 124 of the cover 120, the first partitioning wall 175, the second partitioning wall 176, and the optional at least one additional partitioning wall (not shown), in any suitable manner that enables the second blocking element 191 to engage at least one medical article 163 or a container 160 located in a respective at least one opening 150, so as to hinder the at least one medical article 163 or the container 160 from falling out of the dispenser 100 through the respective opening 150 or being removed from the dispenser 100 from the outside of the cover 120. According to another alternative embodiment, a second blocking element 191 may be fixed to a first wall selected from the first side wall 123 of the cover 120, the second side wall 124 of the cover 120, the optional first partitioning wall 175, the optional second partitioning wall 176 and the optional at least one additional partitioning wall, and protrude towards a second, neighbouring wall selected from the first side wall 123 of the cover 120, the second side wall 124 of the cover 120, the optional first partitioning wall 175, the optional second partitioning wall 176, and the optional at least one additional partitioning wall, in any suitable manner that enables the second blocking element 191 to engage at least one medical article 163 or a container 160 located in a respective opening 150, so as to hinder the at least one medical article 163 or the container 160 from falling out of the dispenser 100 through the respective opening 150 or being removed from the dispenser 100 from the outside of the cover 120.

In a currently preferred embodiment, the at least one second blocking element 191 extends between a set of two neighbouring walls selected from the first side wall 123 of the cover 120, the second side wall 124 of the cover 120, the optional first partitioning wall 175, the optional second partitioning wall 176, and the optional at least one additional partitioning wall, and and is fixed to the set of two neighbouring walls selected from the first side wall 123 of the cover 120, the second side wall 124 of the cover 120, the optional first partitioning wall 175, the optional second partitioning wall 176, and the optional at least one additional partitioning wall, in addition to being fixed to a first edge 183 of a respective first guiding element 180 and protruding from the first surface 180*a* of the first guiding element 180 at an angle z as described in more detail above.

Figure 2E:
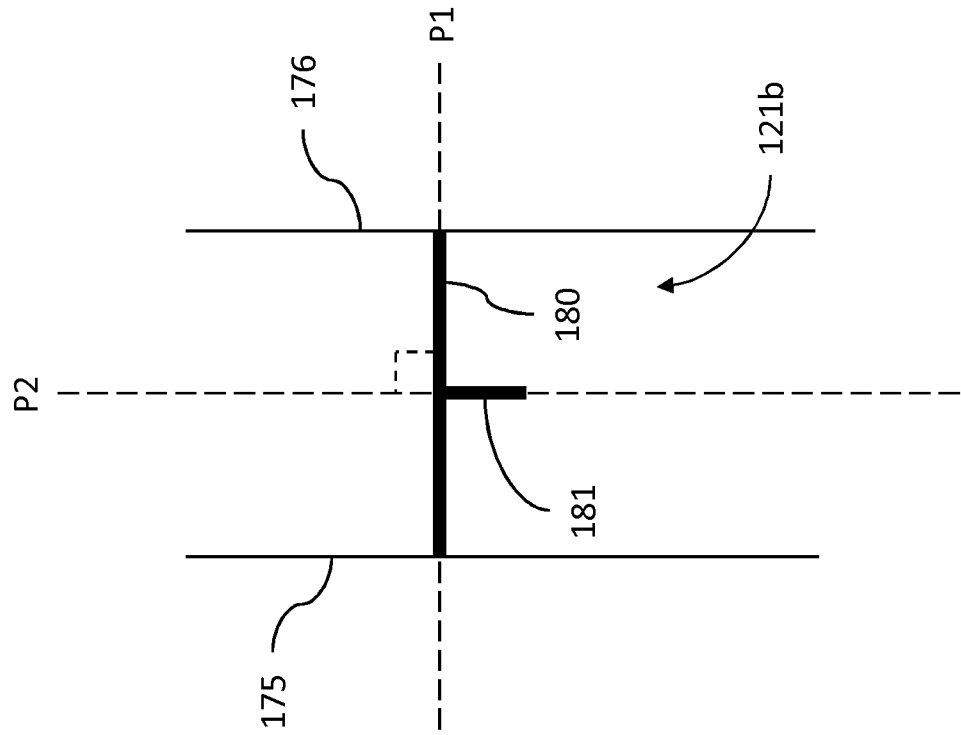
Figure 2D:
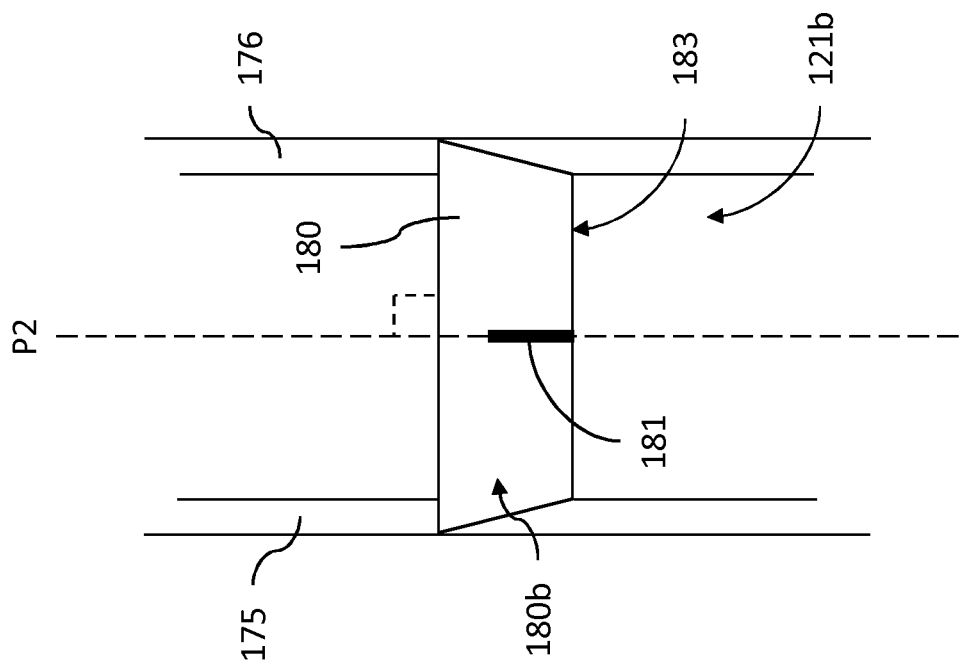

As a non-limiting example, FIG. 2*d* shows a first guiding element 180 extending between a first partitioning wall 175 and a second partitioning wall 176, as viewed at an angle of about 90° to the inside surface 121*b* of the main wall 121 of the cover 120. The first guiding element 180 has a first edge 183. FIG. 2*d* also depicts a second guiding element 181, which protrudes from the second surface 180*b* of the first guiding element 180 in a second plane P2. As described above, a first guiding element 180 may extend between a set of any two neighbouring walls selected from the first side wall 123 of the cover 120, the second side wall 124 of the cover 120, the optional first partitioning wall 175, the optional second partitioning wall 176, and the optional at least one additional partitioning wall. It is to be understood that there is one second plane P2 per two neighbouring partitioning walls. In embodiments of the dispenser 100 where there are at least two second planes P2, the at least two second planes P2 are preferably essentially parallel to each other.

In some embodiments, the second plane P2 is essentially perpendicular to and transversely crossing the first plane P1, which is illustrated in the non-limiting example of FIG. 2*e*.

Figure 3:
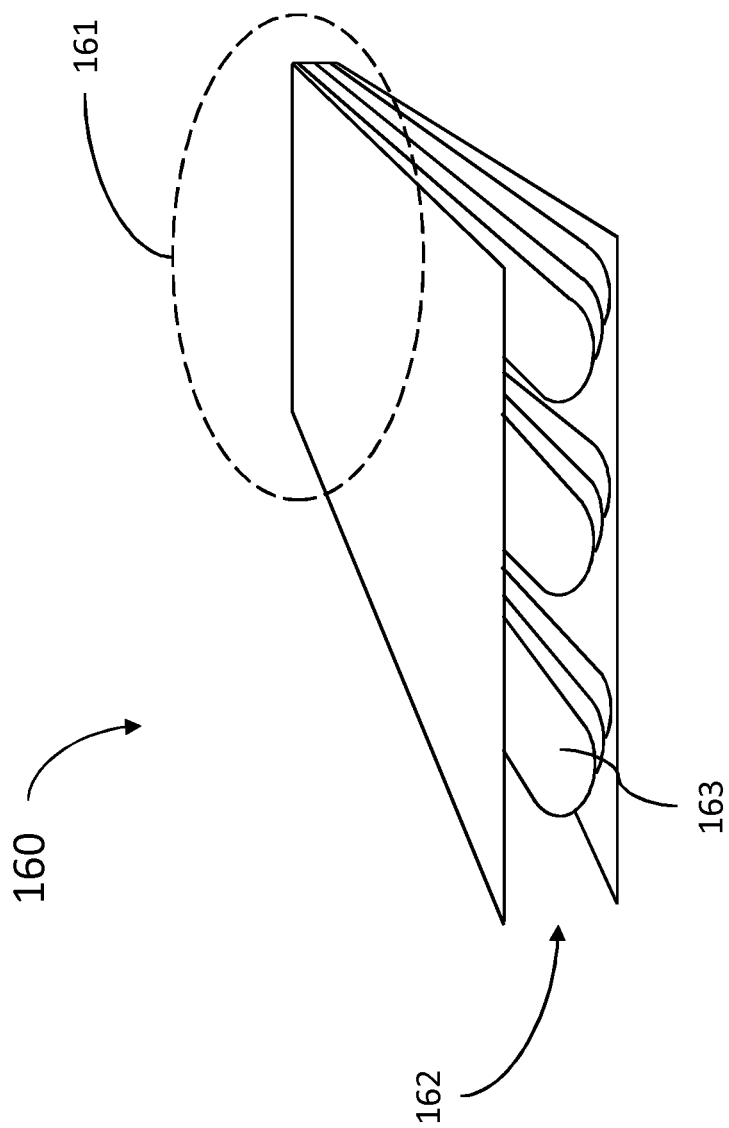
FIG. 3 depicts a non-limiting configuration of a container adapted to hold a plurality of medical articles, which container may be inserted into a dispenser according to the present disclosure.

FIG. 3 depicts a non-limiting configuration of a container 160 adapted to hold one or more medical articles 163, which container 160 may be inserted into a dispenser 100 according to the present disclosure. The container 160 has a back portion 161 and a front opening 162. The at least one opening 150 of the main wall 121 of the cover 120 is configured to receive a container 160, such that the front opening 162 of the container 160 is located in the opening 150 and the back portion 161 of the container 160 extends from the inside surface 121*b* of the main wall 121 of the cover 120, whereby the one or more medical articles 163 are accessible from the outside of the main wall 121 of the cover 120 via the opening 150, both when the dispenser 100 is in a closed configuration and when the dispenser 100 is in an open configuration. Non-limiting examples of medical articles 163 are wound care articles, such as plasters. The back portion 161 of a container 160 may be of any suitable size and shape configured to hold the medical articles 163. A presently preferred shape of a back portion 161 is wedge-formed.

FIG. 4 shows different non-limiting configurations of the inside of a dispenser 100 and different non-limiting configurations of stopper arrangements 170, which are part of a dispenser 100 according to the present disclosure.

Figures 4A, 4B:
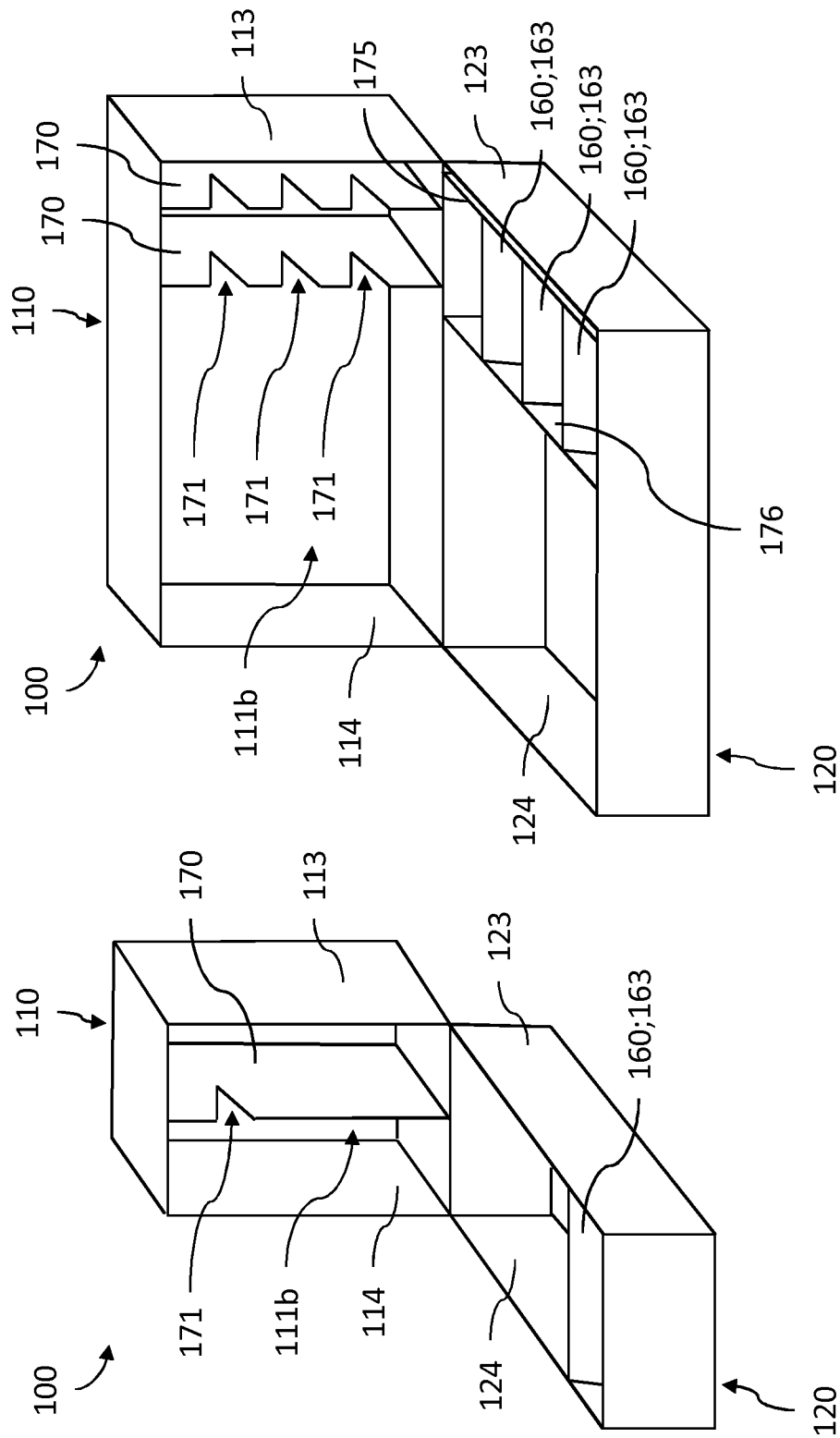
FIG. 4 shows non-limiting configurations of the inside of a dispenser and different non-limiting configurations of stopper arrangements which are part of a dispenser according to the present disclosure.

FIG. 4*a* is a perspective view of an exemplary dispenser 100 as seen from the inside when the dispenser 100 is in an open configuration. According to the present disclosure, the base 110 comprises at least one stopper arrangement 170 integrated in the main wall of the base 110 and protruding from the inside surface 111*b* of the main wall of the base 110, wherein each of the at least one stopper arrangement 170 is configured to hold one or more medical articles 163 and/or containers 160 in place when the dispenser 100 is in a closed configuration (not shown), and wherein each of the at least one stopper arrangement 170 is configured to release its hold on the one or more medical articles 163 and/or containers 160 when the dispenser 100 is in an open configuration, thereby enabling that a medical article 163 and/or a container 160 can be removed from the inside of the cover 120 by use of a single hand grip when the dispenser 100 is in an open configuration. More particularly, each stopper arrangement 170 has at least one cut-out 171 configured to receive and hold at least one medical article 163 or a container 160 received in a respective opening 150 of the main wall 121 of the cover 120 when the dispenser 100 is in a closed configuration, and configured to release its hold on the medical article 163 or the container 160 when the dispenser 100 is in an open configuration. As a non-limiting example, FIG. 4*a* shows one medical article 163 or container 160 being placed between the first side wall 123 and the second side wall 124 of the cover 120, and one stopper arrangement 170 which is configured to hold the medical article 163 or container 160 when the dispenser 100 is in a closed configuration. The at least one stopper arrangement 170 is essential to achieve the main object of the present disclosure, which is to keep a container 160 in place in a respective opening 150 when the dispenser 100 is in the closed configuration while simplifying the removal of a container 160 when the dispenser 100 is in an open configuration.

FIG. 4*b* is a perspective view of a dispenser 100 as seen from the inside when the dispenser 100 is in an open configuration. As a non-limiting example, FIG. 4*b* shows three medical articles 163 and/or containers 160, each of which being received in a respective opening (not shown) extending between a first partitioning wall 175 and a second partitioning wall 176 of the cover 120, such that each of the three medical articles 163 and/or containers 160 are placed between the first partitioning wall 175 and the second partitioning wall 176 of the cover 120. As a non-limiting example, FIG. 4*b* further shows two stopper arrangements 170, each of which being configured to hold the three medical articles 163 or containers 160 when the dispenser 100 is in a closed configuration, and wherein each of the two stopper arrangements 170 is configured to release its hold on the three medical articles 163 and/or containers 160 when the dispenser 100 is in an open configuration. More particularly, each stopper arrangement 170 has three cut-outs 171, each of which being configured to receive and hold a medical article 163 or a container 160 received in a respective opening 150 of the main wall 121 of the cover 120 when the dispenser 100 is in a closed configuration, and being configured to release its hold on the medical article 163 or the container 160 when the dispenser 100 is in an open configuration.

In one or more embodiments, each stopper arrangement 170 has at least one cut-out 171 configured to receive a back portion 161 of a respective container 160 received in a respective opening 150 of the main wall 121 of the cover

120. Turning to FIGS. 4c to 4f, there are shown a number of non-limiting examples of shapes of such cut-outs 171, 171', 171" and back portions 161, 161', 161" of respective containers 160, 160', 160". It is to be understood that FIGS. 4c to 4f are equally applicable to non-limiting examples of shapes of cut-outs 171, 171', 171" configured to receive a portion of at least one respective medical article (163, not shown in FIGS. 4c to 4f) instead of a container 160.

The schematic view of the containers 160, 160', 160" of FIG. 4c illustrates in non-limiting examples that the back portion 161, 161', 161" of a container 160, 160', 160" to be received in a cut-out 171, 171', 171" may be symmetric or asymmetric in shape, and may virtually have any size and shape that is suitable for holding the relevant medical article(s). Although not shown in the figures, it is to be understood that a portion of a medical article 163 to be received in a cut-out 171, 171', 171" may be symmetric or asymmetric in shape, and may virtually have any size and shape.

In the non-limiting examples of FIGS. 4d, 4e, and 4f, the stopper arrangement 170 is illustrated as comprising three cut-outs 171, 171', 171" of different shapes. Of course, a stopper arrangement 170 of a dispenser 100 according to any embodiment presented herein may have one or more cut-outs 171, and if there are two or more cut-outs 171 in a stopper arrangement 170 these may be of the same shape and size, or differ in shape and/or size.

When the dispenser 100 is in the closed configuration, each cut-out 171, 171', 171" is configured to be in contact with at least a part of the back portion 161, 161', 161" of the respective container 160, 160', 160" received in a respective opening 150 of the cover 120. In FIGS. 4d, 4e, and 4f, the cut-out 171 exemplifies a cut-out configured to receive and to be in contact with at least a part of the back portion 161, the cut-out 171' exemplifies a cut-out configured to receive and to be in contact with at least a part of the back portion 161', and the cut-out 171" exemplifies a cut-out configured to receive and to be in contact with at least a part of the back portion 161", respectively. In these illustrational examples, each cut-out 171, 171', 171" is configured to be in contact with at least the upper part of the back portion 161, 161', 161". In some embodiments, as an alternative or as a combination with the above illustrational examples, as illustrated in FIGS. 4d, 4e, and 4f, each cut-out 171, 171', 171" may be configured to enclose at least a part of the closed back portion 161, 161', 161" of the respective container 160 received in a respective opening 150 of the cover 120, or in other words, to be in contact with both an upper part of the back portion 161, 161', 161" and a lower part of the back portion 161, 161', 161". As mentioned above, FIGS. 4c to 4f are equally applicable to non-limiting examples of shapes of cut-outs 171, 171', 171" configured to receive a portion of a respective medical article instead of a container 160, 160', 160".

In one or more embodiments, the part, point, surface or the like of each cut-out 171, 171', 171" that is configured to be in contact with at least a part of a back portion 161, 161', 161" of a respective container 160, 160', 160", and the part of the back portion 161, 161', 161" of the respective container 160, 160', 160" that will come into contact with the part, point, surface or the like of each cut-out 171, 171', 171" are located at an equal distance to the first axis A. Thereby, alignment of the back portion 161, 161', 161" and the respective cut-out 171, 171', 171" is achieved when the dispenser 100 is in the closed configuration, and the workings of the stopper arrangement 170 is improved. Again, FIGS. 4c to 4f are equally applicable to non-limiting examples of shapes of cut-outs 171, 171', 171" configured to receive a portion of a respective medical article (163, not shown in FIGS. 4c to 4f) instead of a container 160, 160', 160".

In the non-limiting examples of FIGS. 4d and 4e, the shape and configuration of the stopper arrangement 170, which is integrated in the main wall 111 of the base of a dispenser according to the present disclosure, creates a distance between the main wall 111 of the base and the innermost point, surface or the like of each cut-out 171,171', 171". In contrast, FIG. 4f shows another non-limiting example in which the innermost point, surface or the like of each cut-out 171,171',171" is part of the main wall 111 of the base of a dispenser according to the present disclosure.

In some embodiments, a stopper arrangement 170 adapted to receive one or more medical articles 163 and/or containers 160 has a serrated or "sawtooth" shape, thereby providing at least one cut-out 171 configured to receive a respective medical article 163 or container 160 received in a respective opening 150 of the cover 120, wherein the portion of the medical article 163 to be received in the cut-out 171, or the back portion 161 of the container 160, is for example wedge-formed.

The cover 120 may optionally comprise at least one second guiding element 181, as shown for example in FIG. 2b, which at least one second guiding element 181 is configured to guide at least one medical article 163 or the back portion 161 of a container 160 into a respective cut-out 171 of a stopper arrangement 170 integrated in the main wall 111 of the base 110 when the dispenser 100 is in the closed configuration.

In some embodiments, the optional second guiding element 181 may have a guiding edge 182, as shown in FIG. 2c, which is configured to guide at least one medical article 163 or the back portion 161 of a container 160 into a respective cut-out 171 of a stopper arrangement 170 integrated in the main wall of the base 110 when the dispenser 100 is in the closed configuration.

In some non-limiting embodiments, the dispenser 100 may comprise a lock which has to be opened to detach the top wall 112 of the base 110 from the top wall 122 of the cover 120, to thereby open the dispenser 100.

In some non-limiting embodiments, the dispenser 100 may comprise a lid, placed on the outside of the cover 120. Such a lid may for example protect any medical articles 163 held in a container 160 placed in an opening 150 of the cover 120 from dirt or moisture.

It is to be understood that the present disclosure is not restricted to the above-described exemplifying embodiments thereof and that several conceivable modifications of the present disclosure are possible within the scope of the following claims. Further, any reference signs present in the claims should not be seen as limiting the extent of the matter protected by the claims; the sole function of such reference signs is to make the claims easier to understand.

The invention claimed is:

1. A dispenser (100) for medical articles (163), comprising:
   a base (110) comprising a main wall (111) having an outside surface (111a) and an inside surface (111b), a top wall (112), a first side wall (113), a second side wall (114), and a bottom wall (115); and
   a cover (120) comprising a main wall (121) having an outside surface (121a) and an inside surface (121b), a top wall (122) having an outside surface (122a) and an inside surface (122b), a first side wall (123), a second side wall (124), and a bottom wall (125); wherein the bottom wall (115) of the base (110) and the bottom wall (125) of the cover (120) are arranged to be attachable to each other, the base (110) and the cover (120), when attached to each other, are arranged to be tiltable in relation to each other around a first axis (A);

the top wall (112) of the base (110) and the top wall (122) of the cover (120) are arranged to be detachably attachable to each other, such that the dispenser is in a closed configuration and the base (110) and cover (120) form a closed space when the top wall (112) of the base (110) and the top wall (122) of the cover (120) are attached to each other, and the dispenser (100) is in an open configuration when the top wall (112) of the base (110) and the top wall (122) of the cover (120) are not attached to each other;

the cover (120) comprises at least one opening (150) in its main wall (121), which at least one opening (150) is adapted to receive at least one medical article (163) or a container (160) configured to hold at least one medical article (163), such that, when at least one medical article (163) or a container (160) comprising at least one medical article (163) is located in an opening (150), the at least one medical article (163) is accessible from the outside of the main wall (121) of the cover (120) via the opening (150);

the base (110) comprises at least one stopper arrangement (170) integrated in the main wall (111) of the base (110) and protruding from the inside surface (111b) of the main wall (111) of the base (110), and each of the at least one stopper arrangement (170) has at least one cut-out (171) configured to receive and hold at least one medical article (163) or a container (160) received in a respective opening (150) of the main wall (121) of the cover (120) when the dispenser (100) is in a closed configuration, and configured to release its hold on the at least one medical article (163) or the container (160) when the dispenser (100) is in an open configuration.

2. The dispenser (100) according to claim 1, wherein the cover (120) optionally comprises a first partitioning wall (175) extending at least a part of the distance between the top wall (122) and the bottom wall (125) of the cover (120), the cover (120) optionally comprises a second partitioning wall (176) extending at least a part of the distance between the top wall (122) and the bottom wall (125) of the cover (120), and one or more of the at least one opening (150) of the main wall (121) extends between two neighbouring walls selected from the first side wall (123) of the cover (120), the second side wall (124) of the cover (120), the optional first partitioning wall (175), and the optional second partitioning wall (176).

3. The dispenser (100) according to claim 2, wherein the cover (120) comprises at least one first guiding element (180) extending in a first plane (P1), the first guiding element (180) having a first surface (180a) facing towards the top wall (122) and a second surface (180b) facing away from the top wall (122), which first surface (180a) of the first guiding element (180) is configured to guide at least one medical article (163) or a container (160) into a respective at least one opening (150) of the main wall (121), and the at least one first guiding element (180) extends between and is fixed to two neighbouring walls selected from the first side wall (123) of the cover (120), the second side wall (124) of the cover (120), the optional first partitioning wall (175), and the optional second partitioning wall (176), at an angle (w) of from 10° to 170°, preferably from 20° to 90°, more preferably from 30° to 70°, to the main wall (121) of the cover (120).

4. The dispenser (100) according to claim 1, wherein the cover (120) comprises at least one first blocking element (190) configured to engage at least one medical article (163) or a container (160) located in a respective at least one opening (150), to hinder the at least one medical article (163) or the container (160) from falling out of the dispenser (100) through the respective opening (150) or being removed from the dispenser (100) from the outside of the cover (120).

5. The dispenser (100) according to claim 3, wherein the cover (120) comprises at least one second guiding element (181), which is fixed to the second surface (180b) of a first guiding element (180), or is fixed to the inside surface (122b) of the top wall (122) and/or to the inside surface (121b) of the main wall (121) of the cover (120), and the at least one second guiding element (181) protrudes from the second surface (180b) of the first guiding element (180), or protrudes from the inside surface (122b) of the top wall (122) and/or from the inside surface (121b) of the main wall (121) of the cover (120), in a second plane (P2), which is essentially perpendicular to and transversely crossing the first plane (P1).

6. The dispenser (100) according to claim 5, wherein the second guiding element (181) has a guiding edge (182) configured to guide at least a portion of a medical article (163) or a back portion (161) of a container (160) into a respective cut-out (171) of a stopper arrangement (170) integrated in the main wall (111) of the base (110) when the dispenser (100) is in the closed configuration, and the guiding edge (182) extends along a second axis (B) at an angle (y) of from 15° to 30°, preferably from 20° to 25°, to the first plane (P1).

7. The dispenser (100) according to claim 4, wherein the cover (120) comprises at least one second blocking element (191) configured to further engage at least one medical article (163) or a container (160) located in a respective at least one opening (150) to hinder the at least one medical article (163) or the container (160) from falling out of the dispenser (100) through the respective opening (150) or being removed from the dispenser (100) from the outside of the cover (120).

8. The dispenser (100) according to claim 1, wherein the cover (120) comprises at least two openings (150) in the main wall (121), and the centers of the at least two openings (150) are located along a third axis (C), which third axis (C) is at an angle (α) of about 90° to the top wall (122) and the bottom wall (125) of the cover (120).

9. The dispenser (100) according to claim 2, wherein the cover (120) comprises at least two openings (150) in the main wall (121), wherein the cover (120) optionally comprises at least one additional partitioning wall extending at least a part of the distance between the top wall (122) and the bottom wall (125) of the cover (120), and a first of the at least two openings (150) extends between a first set of two neighbouring walls selected from the first side wall (123) of the cover (120), the second side wall (124) of the cover (120), the optional first partitioning wall (175), the optional second partitioning wall (176) and the optional at least one additional partitioning wall, and wherein a second of the at least two openings (150) extends between a second set of two neighbouring walls selected from the first side wall (123) of the cover (120), the second side wall (124) of the cover (120), the first partitioning wall (175), the optional second partitioning wall (176) and the optional at least one additional partitioning wall.

10. The dispenser (100) according to claim 1, wherein the at least one cut-out (171) of the at least one stopper arrangement (170) is configured to receive and hold at least a portion of a medical article (163) and/or a back portion (161) of a container (160) received in a respective opening (150) when the dispenser (100) is in the closed configuration, optionally wherein the at least one cut-out (171) is configured to be in contact with at least a portion of a medical article (163) and/or at least a part of the back portion (161) of the respective container (160) received in a respective opening (150), when the dispenser (100) is in the closed configuration.

11. The dispenser (100) according to claim 1, wherein the base (110) is adapted to be mounted on a wall or another at least substantially vertical surface with the top wall (112) of the base (110) located upwards and the bottom wall (115) of the base (110) located downwards in relation to the at least substantially vertical surface, and wherein the bottom wall (125) of the cover (120) is pivotally mounted on the bottom wall (115) of the base (110).

12. The dispenser (100) according to claim 3, wherein the cover (120) comprises at least one first blocking element (190) configured to engage at least one medical article (163) or a container (160) located in a respective at least one opening (150), to hinder the at least one medical article (163) or the container (160) from falling out of the dispenser (100) through the respective opening (150) or being removed from the dispenser (100) from the outside of the cover (120).

13. The dispenser (100) according to claim 2, wherein the cover (120) comprises at least one first blocking element (190) configured to engage at least one medical article (163) or a container (160) located in a respective at least one opening (150), to hinder the at least one medical article (163) or the container (160) from falling out of the dispenser (100) through the respective opening (150) or being removed from the dispenser (100) from the outside of the cover (120).

14. The dispenser (100) according to claim 4, wherein the cover (120) comprises at least one second guiding element (181), which is fixed to the second surface (180*b*) of a first guiding element (180), or is fixed to the inside surface (122*b*) of the top wall (122) and/or to the inside surface (121*b*) of the main wall (121) of the cover (120), and the at least one second guiding element (181) protrudes from the second surface (180*b*) of the first guiding element (180), or protrudes from the inside surface (122*b*) of the top wall (122) and/or from the inside surface (121*b*) of the main wall (121) of the cover (120), in a second plane (P2), which is essentially perpendicular to and transversely crossing the first plane (P1).

15. The dispenser (100) according to claim 13, wherein the cover (120) comprises at least one second guiding element (181), which is fixed to the second surface (180*b*) of a first guiding element (180), or is fixed to the inside surface (122*b*) of the top wall (122) and/or to the inside surface (121*b*) of the main wall (121) of the cover (120), and the at least one second guiding element (181) protrudes from the second surface (180*b*) of the first guiding element (180), or protrudes from the inside surface (122*b*) of the top wall (122) and/or from the inside surface (121*b*) of the main wall (121) of the cover (120), in a second plane (P2), which is essentially perpendicular to and transversely crossing the first plane (P1).

16. The dispenser (100) according to claim 12, wherein the cover (120) comprises at least one second guiding element (181), which is fixed to the second surface (180*b*) of a first guiding element (180), or is fixed to the inside surface (122*b*) of the top wall (122) and/or to the inside surface (121*b*) of the main wall (121) of the cover (120), and the at least one second guiding element (181) protrudes from the second surface (180*b*) of the first guiding element (180), or protrudes from the inside surface (122*b*) of the top wall (122) and/or from the inside surface (121*b*) of the main wall (121) of the cover (120), in a second plane (P2), which is essentially perpendicular to and transversely crossing the first plane (P1).

17. The dispenser (100) according to claim 16, wherein the second guiding element (181) has a guiding edge (182) configured to guide at least a portion of a medical article (163) or a back portion (161) of a container (160) into a respective cut-out (171) of a stopper arrangement (170) integrated in the main wall (111) of the base (110) when the dispenser (100) is in the closed configuration, and the guiding edge (182) extends along a second axis (B) at an angle (y) of from 15° to 30°, preferably from 20° to 25°, to the first plane (P1).

18. The dispenser (100) according to claim 15, wherein the second guiding element (181) has a guiding edge (182) configured to guide at least a portion of a medical article (163) or a back portion (161) of a container (160) into a respective cut-out (171) of a stopper arrangement (170) integrated in the main wall (111) of the base (110) when the dispenser (100) is in the closed configuration, and the guiding edge (182) extends along a second axis (B) at an angle (y) of from 15° to 30°, preferably from 20° to 25°, to the first plane (P1).

19. The dispenser (100) according to claim 14, wherein the second guiding element (181) has a guiding edge (182) configured to guide at least a portion of a medical article (163) or a back portion (161) of a container (160) into a respective cut-out (171) of a stopper arrangement (170) integrated in the main wall (111) of the base (110) when the dispenser (100) is in the closed configuration, and the guiding edge (182) extends along a second axis (B) at an angle (y) of from 15° to 30°, preferably from 20° to 25°, to the first plane (P1).

20. The dispenser (100) according to claim 17, wherein the cover (120) comprises at least one second blocking element (191) configured to further engage at least one medical article (163) or a container (160) located in a respective at least one opening (150) to hinder the at least one medical article (163) or the container (160) from falling out of the dispenser (100) through the respective opening (150) or being removed from the dispenser (100) from the outside of the cover (120).

* * * * *